(12) United States Patent
Grabiner et al.

(10) Patent No.: US 7,980,856 B2
(45) Date of Patent: Jul. 19, 2011

(54) FALL PREVENTION TRAINING SYSTEM AND METHOD USING A DYNAMIC PERTURBATION PLATFORM

(75) Inventors: Mark Grabiner, Chicago, IL (US); Richard Greenwald, Norwich, VT (US); Aaron Buck, Lebanon, NH (US); Jeff Chu, Quechee, VT (US); Robert Palifka, Decatur, GA (US)

(73) Assignee: Simbex LLC, Lebanon, NH (US)

( * ) Notice: Subject to any disclaimer, the term of this patent is extended or adjusted under 35 U.S.C. 154(b) by 1530 days.

(21) Appl. No.: 11/294,942

(22) Filed: Dec. 6, 2005

(65) Prior Publication Data

US 2006/0247104 A1 Nov. 2, 2006

Related U.S. Application Data

(60) Provisional application No. 60/675,768, filed on Apr. 28, 2005.

(51) Int. Cl.
*G09B 19/00* (2006.01)
(52) U.S. Cl. ........................................................ 434/258
(58) Field of Classification Search .................. 434/258; 128/779; 482/8, 9, 900; 600/592, 595, 587; 362/102
See application file for complete search history.

(56) References Cited

U.S. PATENT DOCUMENTS

| | | | |
|---|---|---|---|
| 4,743,008 A | 5/1988 | Fermaglich et al. | |
| 5,052,406 A | 10/1991 | Nashner | |
| 5,209,240 A | 5/1993 | Jain et al. | |
| 5,299,454 A | 4/1994 | Fuglewicz et al. | |
| 5,337,757 A | 8/1994 | Jain et al. | |
| 5,474,087 A | 12/1995 | Nashner | |
| 5,575,294 A * | 11/1996 | Perry et al. | 600/587 |
| 5,582,561 A | 12/1996 | Gonzalez | |
| 5,623,944 A | 4/1997 | Nashner | |
| 5,830,162 A | 11/1998 | Giovannetti | |
| 5,980,429 A | 11/1999 | Nashner | |
| 6,010,465 A | 1/2000 | Nashner | |
| 6,063,046 A | 5/2000 | Allum | |
| 6,162,151 A | 12/2000 | Tani et al. | |
| 6,231,527 B1 * | 5/2001 | Sol | 600/595 |
| 6,436,009 B1 | 8/2002 | Marucci | |
| 6,558,304 B1 | 5/2003 | Bardon et al. | |
| 6,645,126 B1 | 11/2003 | Martin et al. | |
| 6,682,351 B1 | 1/2004 | Abraham-Fuchs et al. | |
| 2002/0115536 A1 | 8/2002 | Hojo et al. | |

OTHER PUBLICATIONS

Jaffe.pdf—'Stepping Over Obstacles to Improve Walking in Individuals With Post Stroke Hemiplegia'—Journal of Rehabilitation Research and Development—May/Jun. 2004—vol. 41, No. 3A, pp. 283-292.*
Shimada Hiroyuki, et al, "New Intervention Program for Preventing Falls Among Frail Elderly People", American Journal of Physical Medicine & Rehabilitation, vol. 83, No. 7, pp. 493-499, Lippincott Williams & Wilkins.

* cited by examiner

*Primary Examiner* — Xuan M Thai
*Assistant Examiner* — Timothy Musselman
(74) *Attorney, Agent, or Firm* — Barlow, Josephs & Holmes, Ltd.

(57) ABSTRACT

A new apparatus, system and method for fall prevention training is provided that delivers, studies and analyzes the biomechanics of a disturbance event, such as a slip or trip incident, so that an appropriate response can be executed by the person to reduce or eliminate the number of falls experienced. The apparatus includes a platform that delivers a disturbance event in less than about 500 ms and preferably in the range of about 100 ms to about 200 ms. The method includes a unique protocol for fall prevention training using the apparatus.

12 Claims, 12 Drawing Sheets

FALL PREVENTION TRAINING SYSTEM AND METHOD USING A DYNAMIC PERTURBATION PLATFORM

CROSS REFERENCE TO RELATED APPLICATION

This application is related to and claims priority from earlier filed provisional patent application Ser. No. 60/675,768, filed Apr. 28, 2005.

BACKGROUND OF THE INVENTION

The present invention generally relates to the medical rehabilitation field. More specifically, the present invention relates to a method for fall prevention training using a dynamic perturbation platform to improve the study and research of the biomechanics of trip, slip, and laterally-directed postural disturbances by a person and the step recovery thereof.

It is well known in the medical field that a slip or trip during walking or standing can lead to a fall and be a serious cause of injury. This is particularly problematic for elderly people where such injuries are a leading cause of mortality. It is well known that many of these injuries can be prevented or their severity lessened if the person uses an effective strategy and technique for responding to a fall situation. Therapeutic Interventions can reduce the likelihood of a fall from a disturbance event, such as a trip or slip incident. Exercise and physical training can be used to develop strength, balance and coordination. Also, the person's environment can be changed to remove obstacles and other hazards that can cause a slip or trip. Bars and hand rails can be provided to assist walking and standing. Padded garments can be worn by the person to reduce the injury caused by the slip or fall.

An alternative approach is to study why a person falls and train them to better recover from a slip or trip to avoid a fall by taking a corrective step response. Therefore, the biomechanics of a slip or fall can be studied to better understand clinically effective ways to prevent such falls due to a slip or trip. As part of the study and analysis of disturbance events, including slip and trip incidents, it is highly desirable to be able to monitor a slip or fall incident in a controlled environment to produce data that is usable for effective training to help persons adapt their strategy for responding to a slip or trip incident.

In view of the foregoing, there is a need for a system that can accurately simulate a slip or tripping incident. There is a need for a system that can measure the biomechanics of a slip or tripping incident to further assist a person to better respond to the incident to avoid a fall. There is a further need for an apparatus that is well-suited to measure such biomechanics. There is a need for an apparatus that can simulate various trip and slip scenarios that could lead to a fall so an appropriate response can be developed. There is a need for an apparatus and system that can better train a person to avoid a fall following a trip or slip incident. Moreover, there is a need for a method for fall prevention training to better prepare a person for a disturbance event, including, a slip, trip or fall, to avoid injury or death.

SUMMARY OF THE INVENTION

The present invention preserves the advantages of prior art fall prevention training systems and methods associated therewith. In addition, it provides new advantages not found in currently available fall prevention training systems and methods and overcomes many disadvantages of such currently available systems and methods.

In accordance with the present invention, a new apparatus and system is provided that studies and analyzes the biomechanics of a disturbance event, such as a slip or trip incident, so that an appropriate response can be executed by the person to reduce or eliminate the number of falls experienced both in real life and in the simulation/disturbance event. With this new apparatus, system and method, a new and novel method for fall prevention training can be delivered which is superior to training methods known in the prior art.

The present invention uses a new and unique disturbance event simulation apparatus. The apparatus, in accordance with the present invention, a perturbation platform is provided which is movable to create a disturbance event that induces a response from an individual. Sensors are located proximate to the individual and the platform with data being outputted from the sensors. A device is provided for collecting and storing the data during the disturbance event. There is also a device for outputting the data so that it may be viewed and studied.

Preferably, the perturbation platform is movable to create the disturbance event in less than 500 ms and more preferably in the range of about 100 ms to about 200 ms. The platform is also preferably a bi-directional motorized belt. Still further, two bi-directional belts can be provided. Also, the apparatus is capable of introducing an obstacle positioned proximate to the platform to induce the response from the individual to the disturbance event. The obstacle, for example, can be a light beam, a three-dimensional object or a hologram.

This unique apparatus can be employed to carry out the new and novel method of fall prevention training of the present invention. The method of fall prevention training of the present invention preferably includes all of the following steps as part of a unique protocol, however, less than all of the steps may be employed and still be within the scope of the present invention. Using the platform of the present invention, from a stop, a sequence of disturbance events are produced with incrementally increasing perturbation distance that establishes a first threshold of that individual's "foot in place" response and not a step response.

Next, from a stop, a sequence of disturbance events are produced with incrementally increasing perturbation distance that establishes a second threshold beyond which the individual can not execute a single step response.

Next, a first obstacle, having a first obstacle height, is placed proximate to the platform at a first obstacle distance to induce the step response of the individual to the disturbance event. From a stop, a sequence of disturbance events are produced with incrementally increasing perturbation distance that establishes a third threshold beyond which the individual can not execute a single step response while attempting to negotiate the obstacle. Further, from a stop, a sequence of the combination of a disturbance event with incrementally increasing perturbation distance are produced followed by a continuous platform motion simulating walking velocity that establishes a fourth threshold beyond which the individual can not achieve a stable gait response.

Next, from a stop, a stable gait response is sought from the individual. If they are able to achieve a stable gait within a predetermined number of steps, the trial is considered successful. If the individual requires more than the predetermined number of steps to achieve stable gait or if the individual falls, the change in velocity is repeated. Trials are be repeated within a session or across sessions until the variability in step response following a given perturbation displacement and profile are below a target value.

Next, a second obstacle, having a second obstacle height, is placed proximate to the platform at a second obstacle distance to induce the step response of the individual to the disturbance event. From a stop, a sequence of a combination of a disturbance event with incrementally increasing perturbation distance is produced followed by a continuous platform motion simulating walking velocity that establishes a fifth threshold beyond which the individual can not achieve a stable gait response. Further, from a first walking velocity created by a continuous platform motion, a sequence of the combination of a disturbance event with incrementally increasing perturbation distance is produced followed by a continuous platform motion returning to the first walking velocity that establishes a sixth threshold beyond which the individual can not achieve a stable gait response.

Next, the individual starts at an initial steady state locomotion velocity with a large disturbance introduced at a random time. The disturbance causes the platform to accelerate to a prescribed disturbance velocity before returning to a second steady state locomotion velocity. The maximum time for this change in the platform velocity is less than about 500 ms, and is more typically in the range of about 100 to about 200 ms. A stable gait response is sought from the individual.

Finally, a third obstacle, having a third obstacle height, is placed proximate to the platform at a third obstacle distance to induce the step response of the individual to the disturbance event. From a second walking velocity created by a continuous platform motion, a sequence of the combination of a disturbance event with incrementally increasing perturbation distance is produced followed by a continuous platform motion returning to the second walking velocity that establishes a seventh threshold beyond which the individual can not achieve a stable gait response.

It is therefore an object of the present invention to provide a new and novel apparatus for use with fall prevention training that more accurately simulates a disturbance event, such as a slip or trip incident, more closely than prior art apparatus.

It is another object of the present invention to provide an apparatus and system that can measure the biomechanics of a disturbance event to further assist a person to better respond to the incident to avoid a fall.

Another object of the invention is to provide an apparatus that is well-suited to measure such biomechanics.

An object of the invention is to provide an apparatus that can simulate various disturbance events that could lead to a fall so an appropriate response can be developed.

A further object of the present invention is to provide a new and novel method for fall prevention training that train a person to avoid a fall when encountered with a disturbance event.

Another object of the present invention is to provide a method for fall prevention training that better prepares an individual for a disturbance event to avoid injury or death.

Yet another object of the present invention is to provide a method for fall prevention training that has a protocol that effectively trains the individual while isolating the weaknesses of the individual.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE PREFERRED EMBODIMENT

Figure 7:
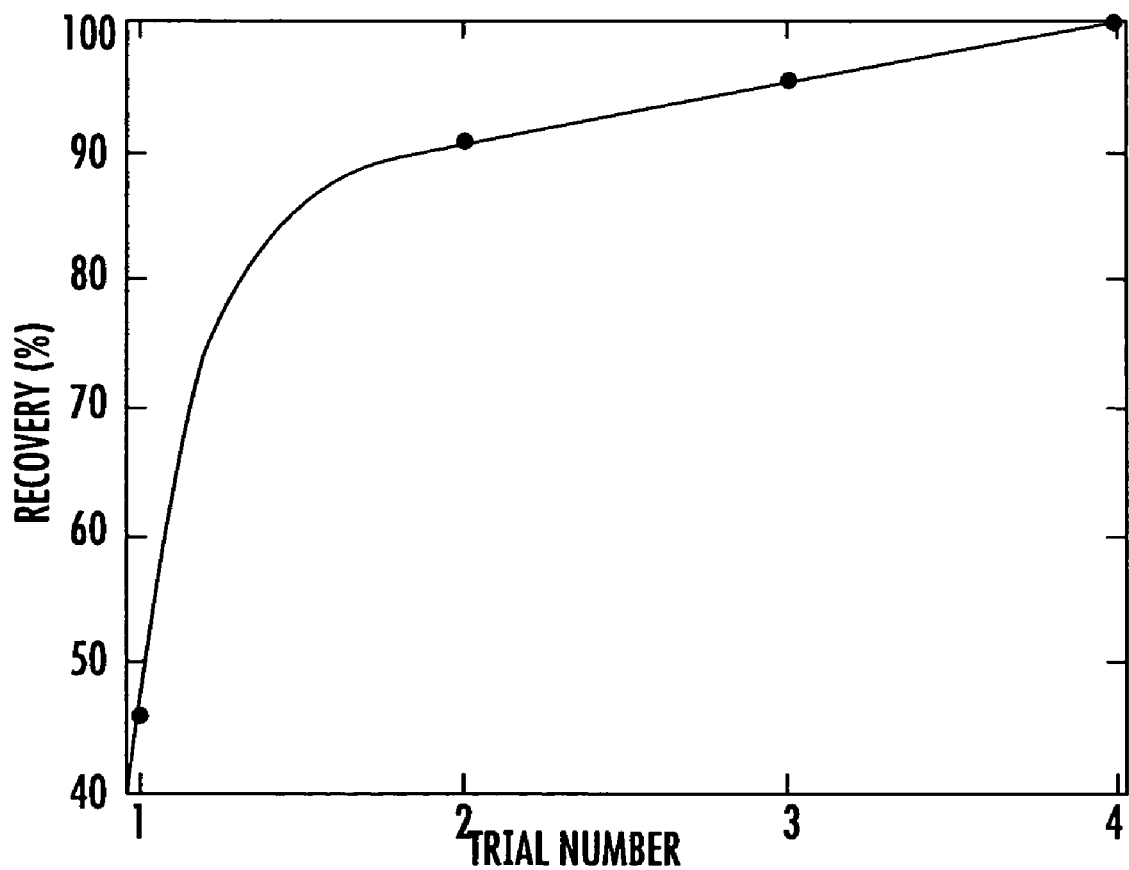
FIG. 7 is a graph showing the increase in recovery percentage in individuals over time as a result of fall prevention training.

The present invention includes a unique method that enables individuals, particularly older adults, to rapidly learn how to modify motor performance and improve recovery rates after being subjected to a disturbance event or perturbation that required a response, such as a step response. The method of the present invention achieves a reduction in the probably of falling by repeated exposure to a realistic disturbance event which serves as targeted and effective motor skill training. As seen in FIG. 7, the recovery percentage increases exponentially over time when they are subjected to trials of fall prevention training. Thus, the method of the present invention provides an invaluable rehabilitation tool for an individual for training how to recover from a large disturbance event, such as a large postural perturbation. To carry out this method, the present invention employs a cost-effective apparatus that can be widely used to reduce the incidence of falling.

The present invention includes a new and novel apparatus and a method which can use that apparatus for fall prevention training. It should be understood that it is preferred that the apparatus of the present invention be used to carry out the method of the present invention. However, the method of the present invention can be carried out by a many different types of training apparatus and still be within the scope of the present invention. The preferred embodiment of the apparatus in accordance with the present invention is set forth in detail below in connection with FIGS. 1-6.

Figure 1:
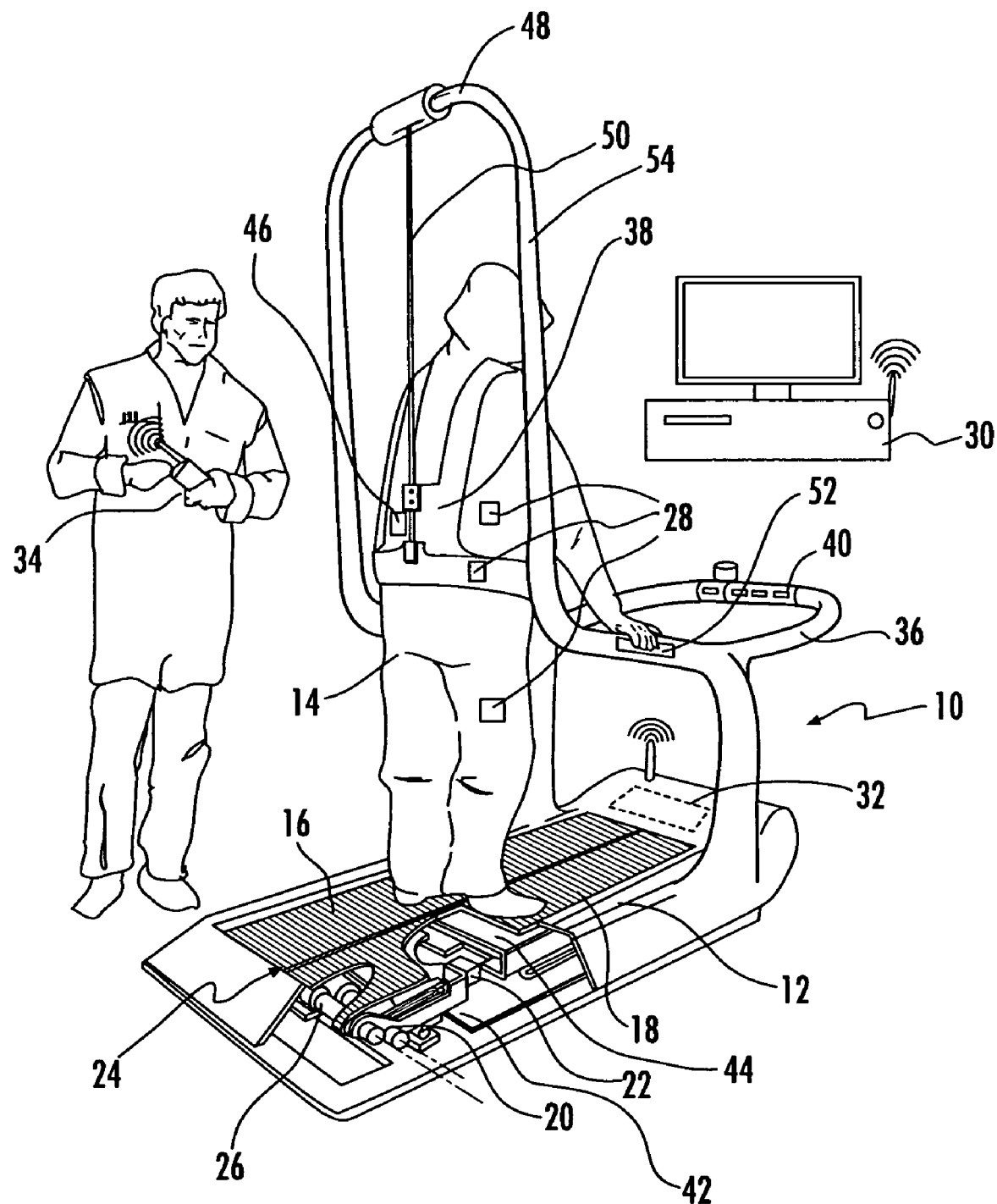
FIG. 1 is a perspective view of the apparatus of the present invention.

Referring first to FIG. 1, an apparatus 10 for use in carrying out the method of the present invention is provided. Preferably, the apparatus 10 is in the form of a force-treadmill perturbation treadmill 12, as shown in FIG. 1, for use in identifying individual risk factors for falling in an individual 14. The following details of the apparatus 10 are preferred to carry out the method. However, it should be understood that many other different types of apparatus 10 can be employed and the components therein can be modified to suit the application at hand. All of these modifications are deemed to be within the scope of the present invention.

The treadmill 12 includes a left belt 16 and a right belt 18, which are both preferably bi-directional for maximum control and timing of belt position, velocity and acceleration. For example, each belt 16, 18 preferably has bi-directional displacement control for large perturbations from 6 mm (0.25 in) to infinity (continuous operation) with minimum 6 mm (0.25 in) resolution. The belts 16, 18 also have bi-directional velocity control from 0-4 m/s (~9 mph) and bi-directional acceleration control from 0-6 m/s$^2$. The belts 16, 18 are critically tuned to avoid oscillations. As far as preferred dimensions, each belt 16, 18 is approximately 250 mm (~10 in) wide with a platform length of approximately 1.6 m (5 ft). It is also possible that a single belt (not shown) may be used instead of the dual belts 16, 18 shown in FIG. 1.

The apparatus 10 also includes a motor and drive system 20. A high torque direct drive motor is preferred although other drive systems 20 may be used. Motors for driving belts are well known in the art and need not be discussed further therein.

Most importantly, the apparatus 10 is configured to create the disturbance event in less than 500 ms. More preferably, the disturbance event is created in the range of about 100 to about 200 ms. The creation of the disturbance event, such a movement of a belt 16 or 18, at such a fast speed is not found in the prior art. The relatively short duration of the disturbance event is used so that it simulates a real disturbance event to trigger a more accurate response from the individual 14.

Figure 6:
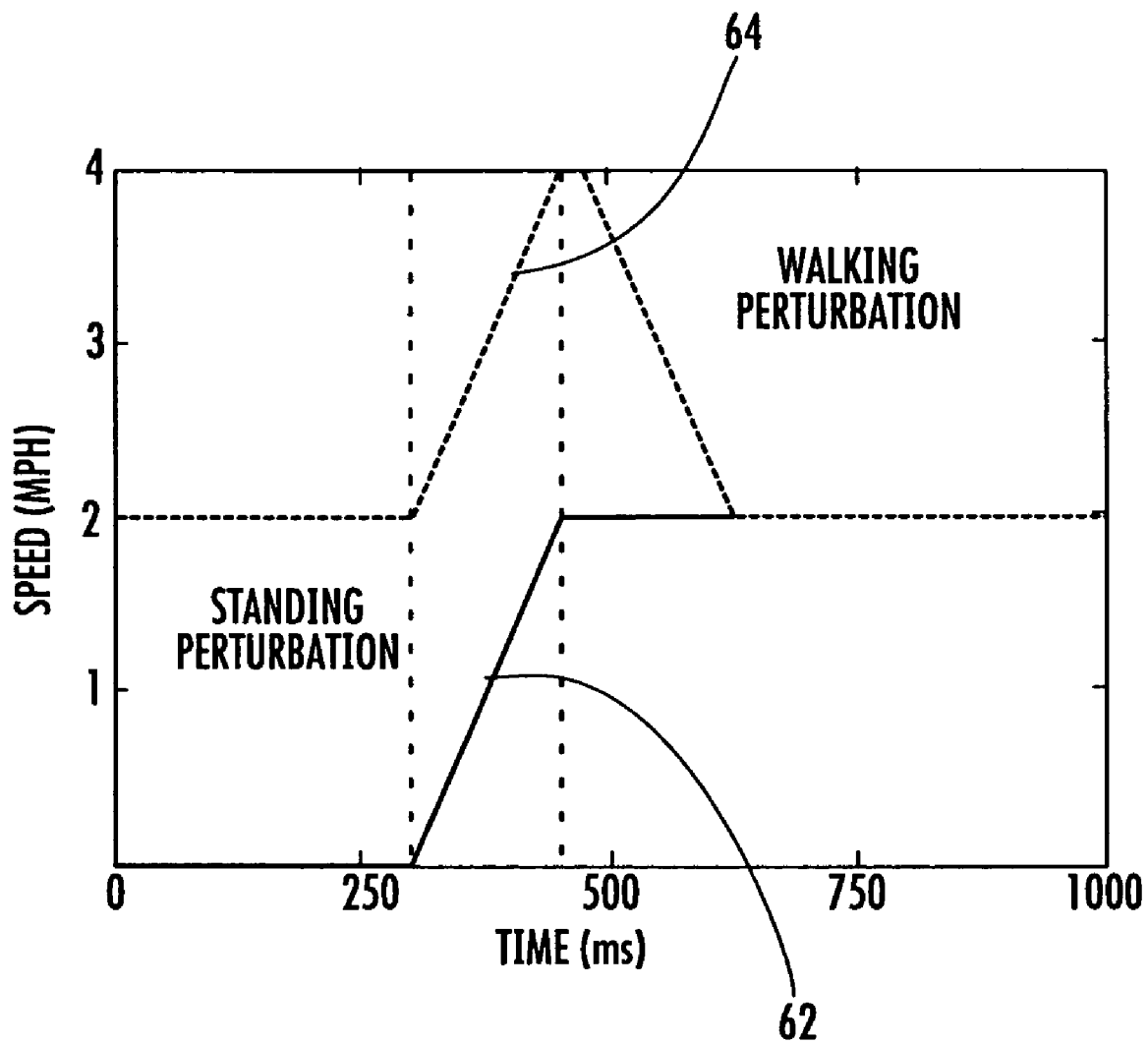
FIG. 6 is a graph showing speed against time for executing a standing and walking perturbation in accordance with the present invention.

FIG. 6 is a graph of the speed of a belt 16, 18 against time to illustrate the unique fast creation of a disturbance event. Line 62 represents the speed of creation of a disturbance event for a standing perturbation where the individual 14 is standing still and belts 16, 18 are ramped up to a 2 MPH speed in the range of about 100 to about 200 ms. Similarly, line 64 Line 64 represents the speed of creation of a disturbance event for a walking perturbation where the individual 14 is walking at about 2 MPH and belts 16, 18 are accelerated over 4 MPH in the range of about 100 to about 200 ms.

Further, multi-axis load transducers 22, such as low-profile multi-axis load cells with desired range, accuracy, and sensitivity, which support the platform, generally referred to as 24 of treadmill 12, and drums 26 of the treadmill apparatus 12. The pressure applied by an individual 14 to the bed of the platform 24 can be measured with such pressure transducers 22.

Figure 5:
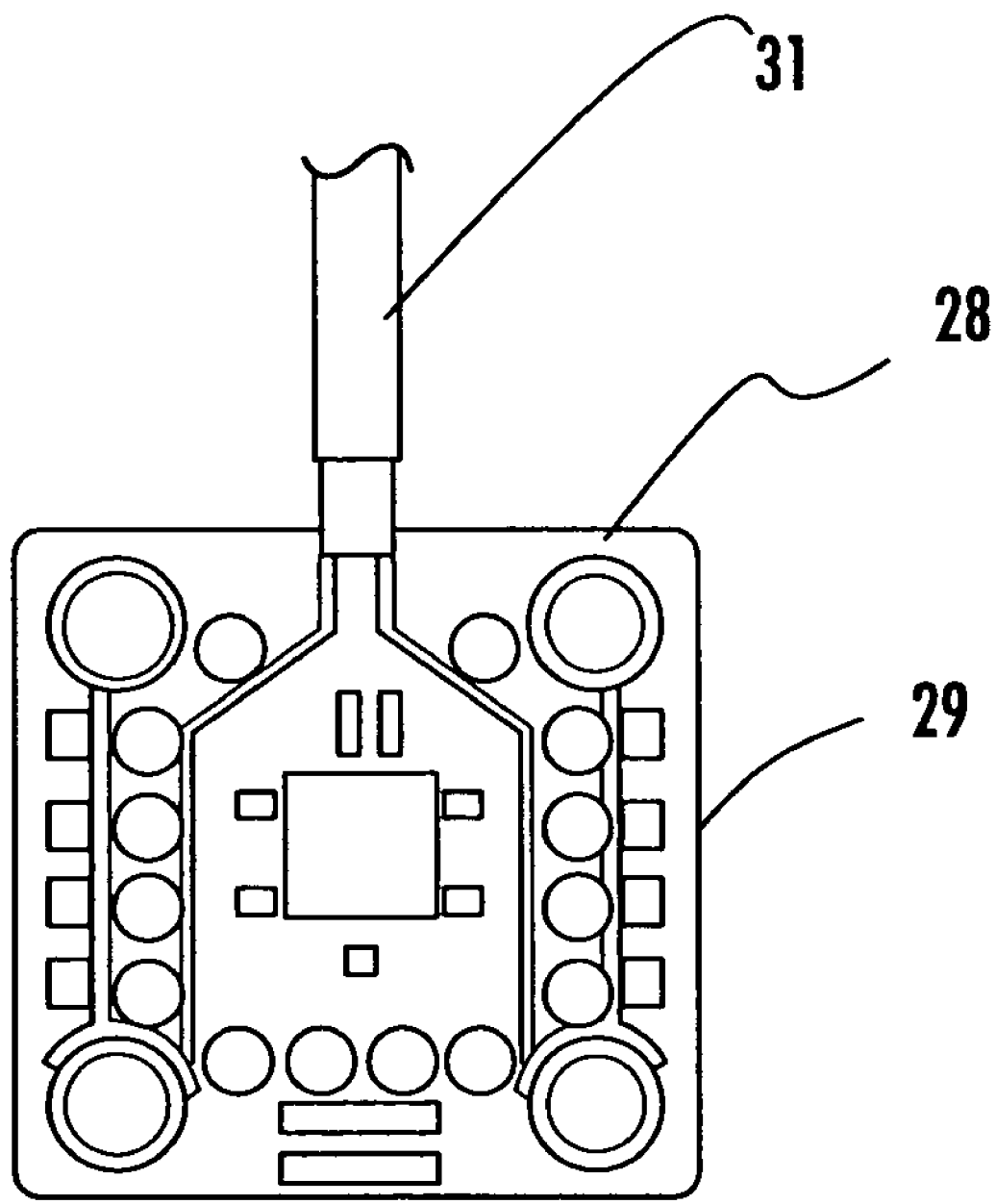
FIG. 5 is a top plan view of an inertial sensor used in the present invention.

The apparatus 10 of the present invention also includes a number of sensors 28 that are attached the individual 14 that is being trained and optionally at various locations on the apparatus 10 itself. For example, inertial sensors 28, which are well known in the art, can be placed on various parts of the body of the individual 14 to sense position and velocity. An example of a prior art inertial sensor 28 is shown in FIG. 5 with circuit board 29 and electrical lead 31. As a further example, an inertial sensor 28 can be positioned on the trunk of the individual 14 to sense trunk angle and velocity, which are important factors to be studied in connection with fall prevention training. While sensors 28 are preferred, other ways to measure body location can be used, such as video analysis of body movement.

Sensors located between the underside of the belts and the deck of the apparatus sense the location of the subject's foot as it contacts the platform. This plurality of sensors is preferably in an array with a sensing element every 1 cm in both the length and width direction of the apparatus. In the preferred embodiment, these sensing elements are made, for example, from a thin pressure sensitive material and are contact sensors whose electrical output is triggered when foot contact pressure to the sensor through the belt exceeds a certain pre-determined level. While this array of thin contact sensing elements is the preferred embodiment, these sensing elements could also produce a voltage whose output was proportional to applied pressure or force. Also, while thin pressure sensitive material is preferred, any type of sensors, which can be either of the digital ON/OFF or proportional analog, can also be used in accordance with the present invention.

The sensors 28 gather data regarding the various parameters that are being monitored. This data is, preferably in real-time, sent to a computer 30 for processing and analysis. The data may be sent to the computer 30 wirelessly or by hard wire. Data transmission and computer processing devices are so well known in the art that they need not be discussed in further detail herein.

The apparatus 10 itself preferably includes its own central control unit 32 with the appropriate control algorithm and custom motor control software, which provides bilateral, independent bi-directional real-time biofeedback motor control function. The control algorithm is written as a state machine, and responds according to a lookup-table of inputs to determine the next step. A radio frequency (RF) telemetry console 34 is used for many operational functions of the apparatus 10, including programming and operation of handrails 36, safety harness 38, and emergency stop switch 40. The control algorithm is preferably written in C using LabWindows CVI software and, where appropriate, native microcontroller firmware language. The key elements of the control system 32 include encoders attached to drive motors provide data for motion control of the platform 24 and PID algorithms for smooth, accurate motion. Also, the control system handles triggering of perturbations at specific times during the walking cycle based on force measurements and monitoring and recording of step recovery response and appropriate state-machine response to inputs. There are also safety interlocks to protect the individual 14. Thus, the treadmill apparatus 10 of the present invention includes two main components, the perturbation platform (PPU) 24 with force measurement capability, safety harness 38 and handrails 36 as well as a central control unit (CCU) 32 with control algorithms, safety interlocks, data storage and transfer protocols, and user interface.

Referring back to FIG. 1, the treadmill apparatus 10 includes a frame 42 to integrate the platforms on the underside of each transducer and provide rigid attachment points for the mounting of the treadmill 10 to the ground. The frame 42 is designed to minimize any mechanical crosstalk that may be induced by the use of a common frame. The belts 16, 18 and platforms 44 thereunder are separated by a physical width of 0.125 in. to minimize any influence two separate belts 16, 18 may have on gait patterns of the individual 14 during walking while preventing any belt overlap that may occur.

The apparatus 10, which includes a motor controller and amplifier with associated electronics within the CCU 32, is preferably PC based with cabling to the amplifiers to enable a development environment for testing.

The apparatus 10, as seen in FIG. 1, also includes a harness system 38 that embraces the individual 14 and is suspended from support bar 48 via tether 50. Support bar 48 is positioned by vertical posts 54. Force transducers 46, mounted in the training harness 38, generate use input signals to determine when an individual 14 has fallen. The harness 38 is used as both a safety subsystem and as a control input device to system software, and is integrally attached to the platform 24 through the subsystem frame. Known chest harnesses (e.g. climbing chest harness) are integrated to the subsystem frame using tubular steel. Further, low-profile handrails 36 are included as a safety feature. The handrails 36 are attached to the treadmill 12 base in such a way that the force transducers 52 can identify and quantify when the rails 36 are being used to support the individual's body weight. This data is also used for real-time biofeedback control of the treadmill 12. Powder coated bent tubular steel and powder coated for each rail 36, 54 is preferred although other handrail constructions may be used.

Software modules are an important component of the apparatus and control thereof of the present invention. Software modules are preferably developed in a high level language, such a C, but are designed for implementation on an embedded microcontroller or dedicated microprocessor. Computational modules are also employed for kinematic measurements derived from numerous markers placed on the body for computations of stepping response to large postural perturbations. For example, 26 markers on the body of the individual 14 may be used. These measures, including trunk angle and trunk velocity, are of assistance to discriminate fallers versus non-fallers.

It should be understood that each of the foregoing components are preferably included in the apparatus 10 of the present invention. However some components and features may be omitted from the apparatus and still be within the scope of the present invention. For example, the apparatus 10 employs force transducers 44, 46, 54, however, such force measurements may not be required for the analysis of the kinetic data in order to be effective as a training tool. For example, it may be sufficient to have programmed control algorithms and relatively simple sensing capabilities that perform universal protocols.

Figure 2:
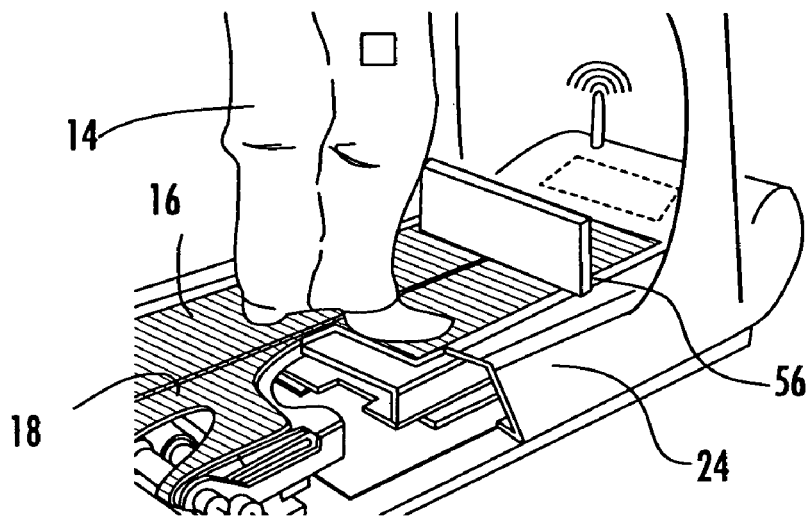
FIG. 2 is a close-up perspective view of the apparatus of the present invention equipped with a physical obstacle.
Figure 3:
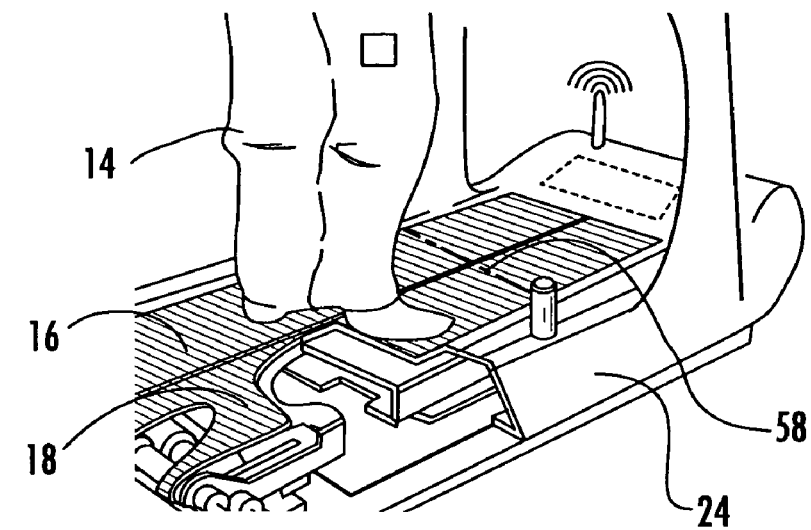
FIG. 3 is a close-up perspective view of the apparatus of the present invention equipped with a virtual obstacle in the form of a laser beam.
Figure 4:
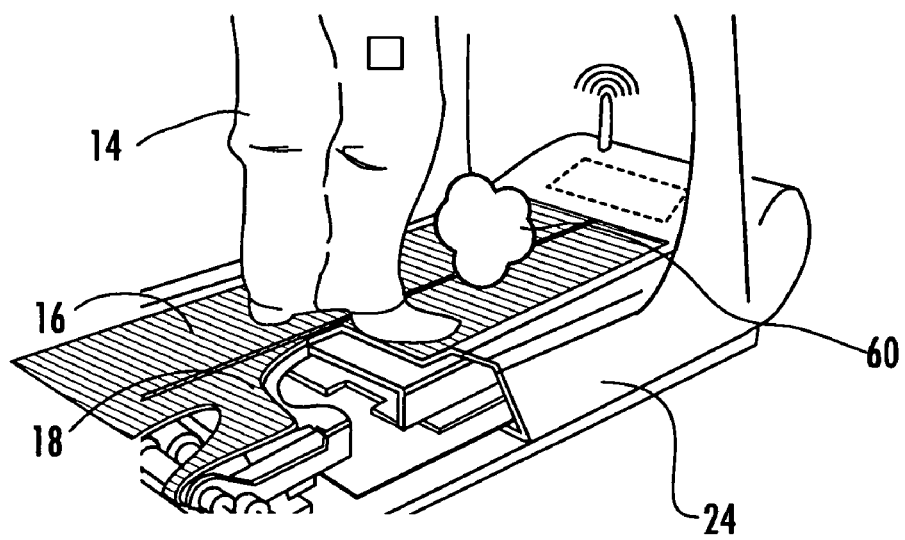
FIG. 4 is a close-up perspective view of the apparatus of the present invention equipped with a virtual obstacle in the form of a hologram.

Referring now to FIGS. 2-4, the optional use of obstacles with the apparatus 10 of the present invention. The use of such obstacles in the method of training of the present invention improves the overall effectiveness thereof. In FIG. 2, the treadmill 24 is equipped with a physical obstacle 56 that is placed proximate to the individual. For example, the obstacle 56 is a wall or barrier that is place in front of the walking path of the individual 14. This obstacle 56 may be place above the belts 16, 18 or may be placed directly thereon. Or, the obstacle 56 may, upon command, emanate upwardly from the platform 24 to then be proximate to the individual 14.

In FIG. 3, the obstacle employed, in this embodiment, is a laser beam 58 that passes proximate to the individual 14, namely, in their walking path. Still further, in FIG. 4, the obstacle employed, in this embodiment, is a hologram 60. As will be discussed below, in connection with the method of the present invention, the obstacles 56, 58 and 60 play an important role in training the individual 14. The obstacles 56, 58 and 60 simulate real obstacles that may be faced in a real world non-training setting. The virtual obstacles 58 and 60 may also be used to sense when the individual 14 passes therethrough to serve as an additional sensor.

In view of the foregoing, the apparatus 10 of the present invention can measure an individual's step response to a disturbance event, such as trip or slip incident. Therefore, it can be used to evaluate tripping and slipping fall mechanism in anterior and posterior directions. It can also evaluate stepping responses from static positions in the anterior, posterior and lateral directions. Recovery strategies can also be evaluated to reduce occurrences of falls. The complete measurement and computational capabilities of the present invention enables specific individual risk factors to be identified so appropriate training can be developed and carried out to better avoid fall incidents. Thus, novel biomechanical factors can be linked to the prediction and prevention of falling with better accuracy and effectiveness than prior art devices and systems.

The data obtained from the system and apparatus of the present invention can then be used to better train a person for a fall in accordance with the new method for fall prevention training of the present invention. As discussed in detail below, the apparatus 10 can be used to execute a unique protocol of fall prevention training that teaches a person how to better react to a disturbance event according to strategies learned from the apparatus and system described above. For example, a succession of simulated trip incidents can be delivered where the velocities and/or accelerations or a combination thereof of each successive event is built up over time to lead up to a trip situation. By using the unique apparatus 10 of the present invention, a method of training can be delivered where a slip incident can be generated from a static position. This simulates a condition where an individual loses their balance when standing still.

Also, and most importantly, the present invention can generate a dynamic slip or trip condition where a second velocity is delivery after a first velocity has been delivered. This simulates a condition where the individual is walking (corresponding to the first velocity) and then encounters a trip or slip situation while walking. Thus, a change of velocities can be delivered to better simulate various conditions that cannot be simulated with prior art devices. Such a method of training is preferably carried out using the apparatus of the present invention described above.

Referring now to FIGS. 8-14, details of the method of fall prevention training is shown and described in detail. The method of the present invention provides a protocol to execute and carry out the fall prevention training of the present invention. This is a general protocol employed in the method of the present invention and can be applied to any of the large disturbance events used in the present method of training. As will be discussed in detail below, the method is a multi-stage process that outlines a unique training progression that is used in an attempt to reduce the incidence of falls by an individual. While this is a preferred method, there is no set number of cycles or limits. In general, the method uses a unique protocol that requires the individual to achieve a goal to represent the acquisition of a given skill. Moreover, multiple trials at a given disturbance level represents skill retention and the results of future retesting indicates skill decay.

Stage 1—Small Disturbance, No Step Response

Figure 8:
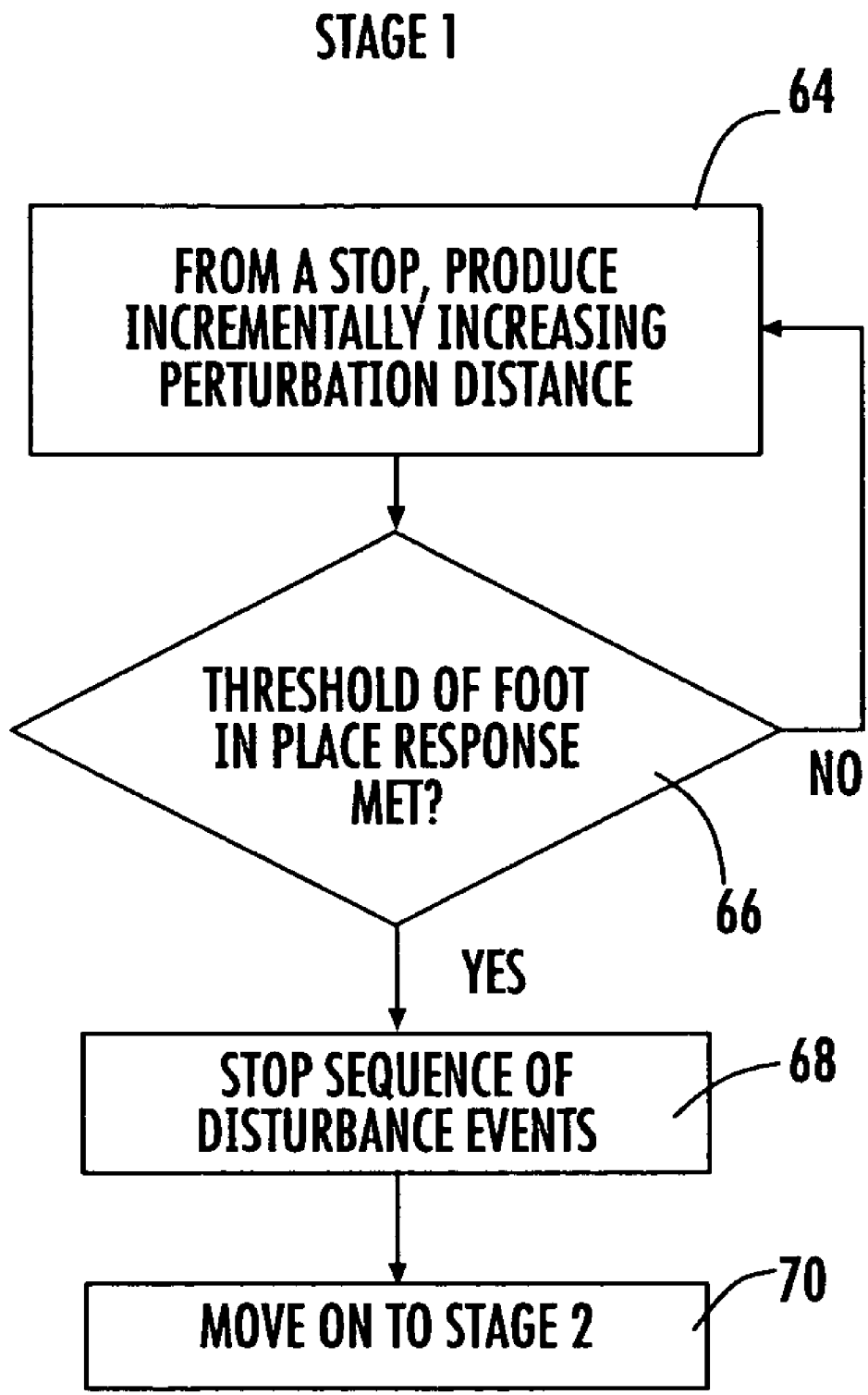
FIG. 8 is a flow chart illustrating the execution of Stage 1 of the method of the present invention.

As represented by FIG. 8, in the first stage of the protocol, the individual 14 stands with two feet on platform. A small disturbance is introduced at a random time. The platform moves a finite distance and stops. As stated above, the platform moves in less than about 500 ms and, preferably, in the range of about 100 ms to about 200 ms to ensure a realistic disturbance event. The disturbance level in Stage 1 should be small to determine if the individual can use respond to the disturbance with what is commonly referred to as a "feet in place" recovery strategy. This means that the individual adopts a recovery strategy that maintains upright posture and which requires minimal movement of the feet (e.g. no step response).

For example, the individual might use what is referred to as an "ankle strategy" or a "hip strategy" whereby the individual alters their ankle and/or hip rotation angle in one or more directions and stabilizes their body with their muscles with no step response. At this stage, the perturbation distance preferably remains the same until the individual has shown that their response is low in variability.

The perturbation distance incrementally increases at 64 as the individual successfully completes the feet in-place response. This increase in distance continues until the individual is able to complete a prescribed distance, or threshold, which is determined based on intrinsic parameters of the individual, such as height, body center of mass, age, and flexibility. Once the individual has exceeded the predetermined maximum perturbation threshold without a step response at 66, the sequence of disturbance events are stopped at 68 and they are moved to the Stage 2 in the protocol at 70.

Stage 2—Step Response to Large Perturbation

Figure 9:
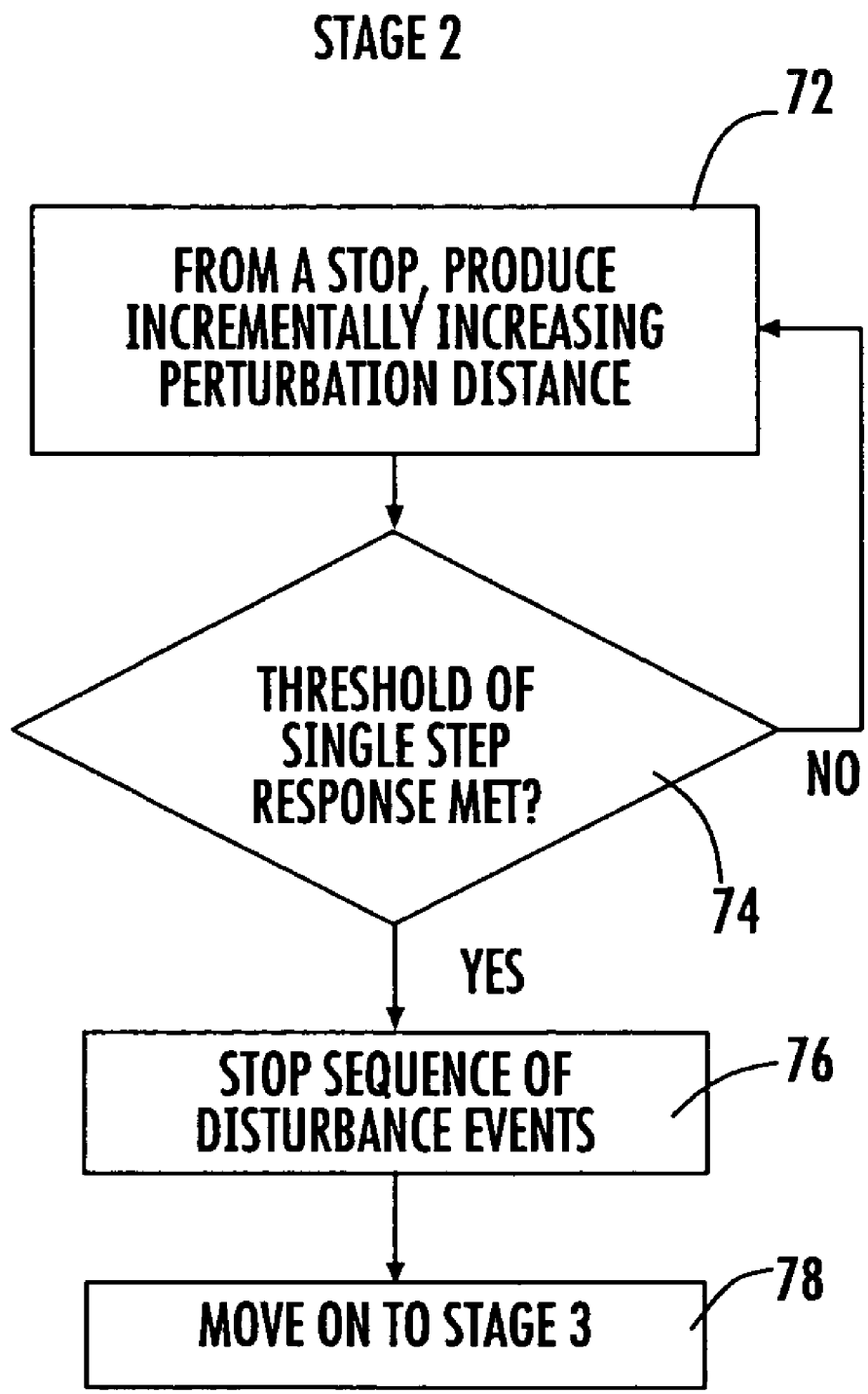
FIG. 9 is a flow chart illustrating the execution of Stage 2 of the method of the present invention.

In FIG. 9, the individual starts at a standstill and a large disturbance is introduced at a random time. The platform moves a finite distance and stops. The disturbance magnitude preferably exceeds the magnitude of the maximum disturbance in Stage 1 above. The maximum time for this displacement of the disturbance to occur is less than 500 ms, and is more typically in the range of about 100 to about 200 ms, and preferably about 250 ms.

In Stage 2, a single step response by the individual is sought. If the individual is able to maintain posture with a single step, the given train within Stage 2 is considered successful. If the individual requires more than one step to maintain posture or falls, the perturbation distance is repeated.

Trials are be repeated within a session or across sessions until the variability in step response following a given perturbation displacement and profile are below a target value. For example, a minimization function relating step length and step width might be employed to calculate a residual value for step response. This value is called a target step response. The variance in this computed value for a given trial compared to the previous n trials can be used. Alternative methods of determining a threshold for success for step response to a given perturbation are readily defined, such as the number of trials in a row for achieving the target step response required by Stage 2.

After an individual successfully passes the single step response test for a given perturbation distance and acceptably low variability between sessions, that distance is increased at 72 until individual is able to complete a prescribed perturbation distance threshold at 74. In similar fashion to Stage 1, intrinsic parameters of the individual, such as height, body center of mass, age, and flexibility, are used to determine a maximum perturbation distance, or threshold, for that individual. Once the individual has exceeded the predetermined maximum perturbation with only a single step response, the sequence of disturbance events are stopped at 76 and they are moved to the Stage 3 in the protocol of the method of the present invention at 78.

Stage 3—Step Response with First Obstacle

Figure 10:
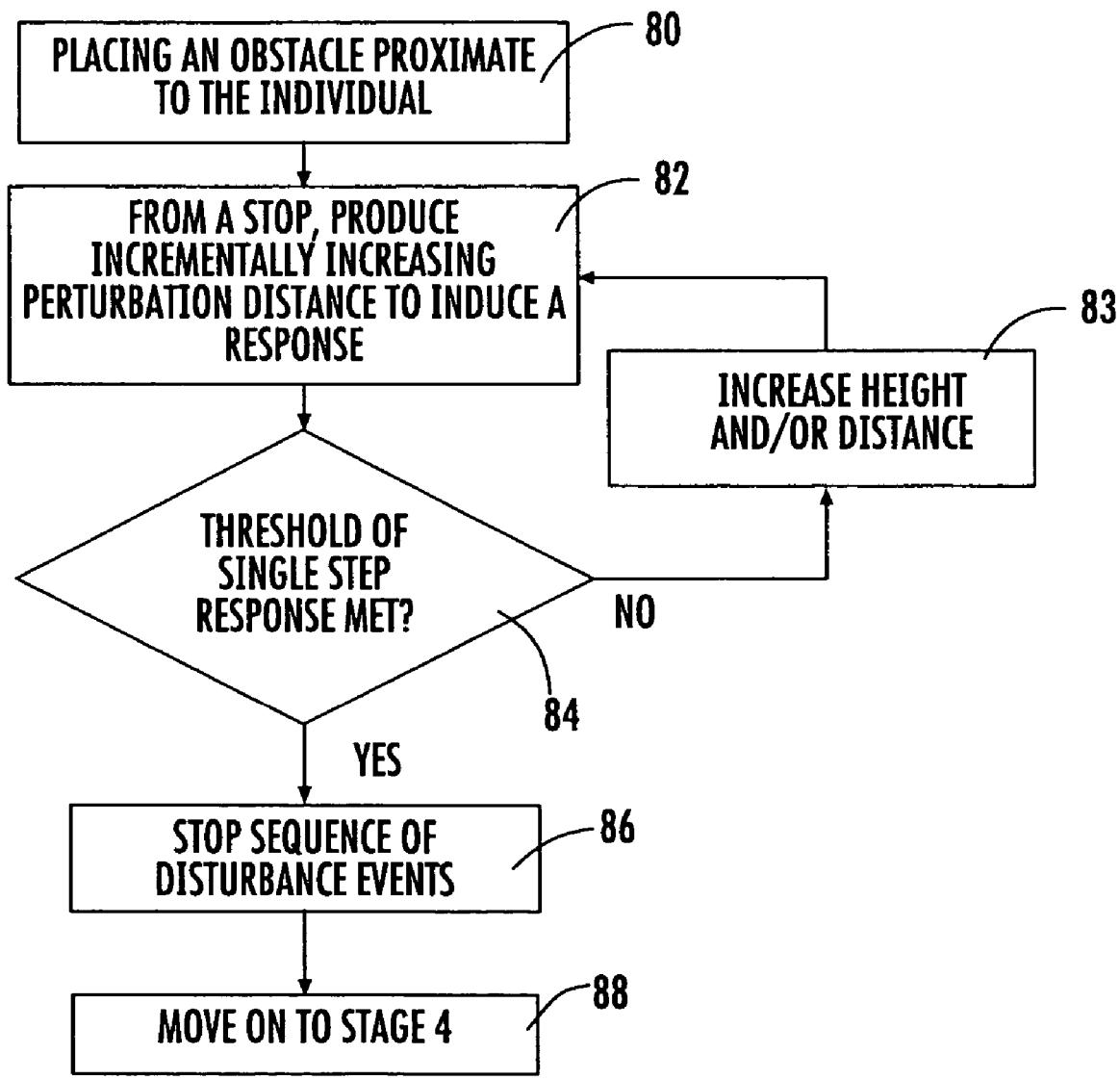
FIG. 10 is a flow chart illustrating the execution of Stage 3 of the method of the present invention.

In FIG. 10, the individual starts at a standstill. A first obstacle is placed proximate to the individual at 80, such as ahead of the individual in the direction, so that the perturbation forces them to make a step response. A large disturbance is also introduced at a random time. The platform moves a finite distance and stops. The disturbance magnitude exceeds the magnitude of the maximum disturbance in Stage 1. The maximum time for this displacement of the disturbance to occur is less than about 500 ms, and is more typically in the range of about 100 to about 200 ms.

The distance and position that the first obstacle is placed from the individual can vary between zero (i.e. touching the individual) and a prescribed maximum obstacle distance from individual. Intrinsic individual parameters, such as height and body center of mass, are used to determine a maximum obstacle distance from individual for that individual. The obstacle can either be real or virtual. For example, the obstacle, which may be made from any material, may be a barrier or wall that emanates up from the floor of the platform. Such an obstacle may be driven by springs or actuators to control its positioning proximate to the individual. For virtual obstacles, 3-D holograms and laser beam systems are a few examples. In the preferred embodiment of the present invention, the obstacle is 5 cm high but it could be of any height. For example, the obstacle may be in the range of only about 1 mm up to about one half of the body height of the individual.

A single step response is sought from the individual. If they are able to negotiate the obstacle and to maintain posture with a single step, the trial is considered successful. If the individual requires more than one step to maintain posture or falls, the perturbation distance is repeated.

Trials are repeated within a session or across sessions until the variability in step response following a given perturbation displacement and profile are below a target value. For example, a minimization function relating step length and step width might be employed to calculate a residual value for step response. This value is called a target step response. The variance in this computed value for a given trial are compared to the previous n trials can be used. Alternative methods of determining a threshold for success for step response at 84 to a given perturbation are readily defined, such as the number of trials in a row for achieving the target step response.

After a individual successfully passes the single step response test for a given perturbation distance, that distance is incrementally increased at 82 until individual is able to complete a prescribed distance. Also, the height of the obstacle is progressively increased at 83 up to a prescribed height and the initial distance of the obstacle from the individual is progressively increased up to a prescribed perturbation distance.

The intrinsic individual parameters, such as height, body center of mass, age, and flexibility, are used to determine a maximum perturbation distance for that individual, the maximum obstacle height for that individual and the maximum initial obstacle distance for the individual. Once the individual has exceeded the predetermined maximum perturbation, with only a single step response and acceptably low variability between sessions, the disturbance events are stopped at 86 and they are moved to the Stage 4 at 88 in the protocol outlined below. It should be noted that in the case where the disturbance event is intended to be large and to simulate a slip incident, Stage 3 may be omitted.

Stage 4—Stable Gait after Standstill

Figure 11:
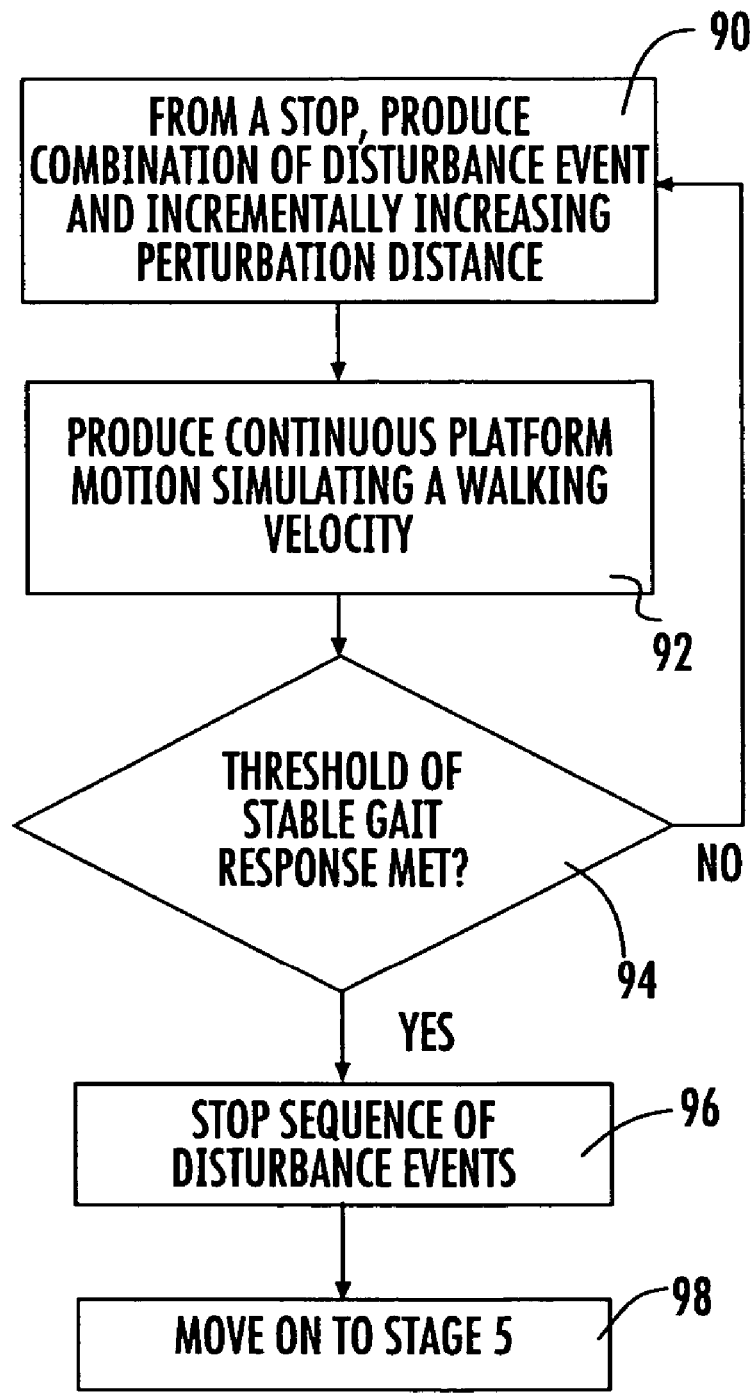
FIG. 11 is a flow chart illustrating the execution of Stage 4 of the method of the present invention.

In FIG. 11, the individual 14 starts at a standstill and a large disturbance is introduced at a random time. The disturbance causes the platform to accelerate to a prescribed (non-zero) velocity. This second velocity is called the velocity change. The maximum time for this change in the platform velocity is less than about 500 ms, and is more typically in the range of about 100 to about 200 ms.

A stable gait response is sought from the individual. If they are able to achieve a stable gait within a predetermined number of steps, the trial is considered successful. If the individual requires more than the predetermined number of steps to achieve stable gait or if the individual falls, the change in velocity is repeated. Trials are be repeated within a session or across sessions until the variability in step response following a given perturbation displacement and profile are below a target value.

For example, a minimization function relating step length and step width might be employed to calculate a residual value for step response. This value is called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity change perturbation, that velocity change is incrementally increased at 90 to produce continuous walking at 92 until individual is able to successfully complete a prescribed velocity change. Intrinsic individual parameters, such as height, body center of mass, age, and flexibility, are used to determine a maximum velocity change threshold at 94 for that individual. Once the individual has exceeded the predetermined maximum velocity change with stable gait step response and acceptably low variability between sessions, the disturbance events are stopped at 96 and they are moved to the Stage 5 in the protocol at 98.

Stage 5—Stable Gait After Standstill with Second Obstacle

Figure 12:
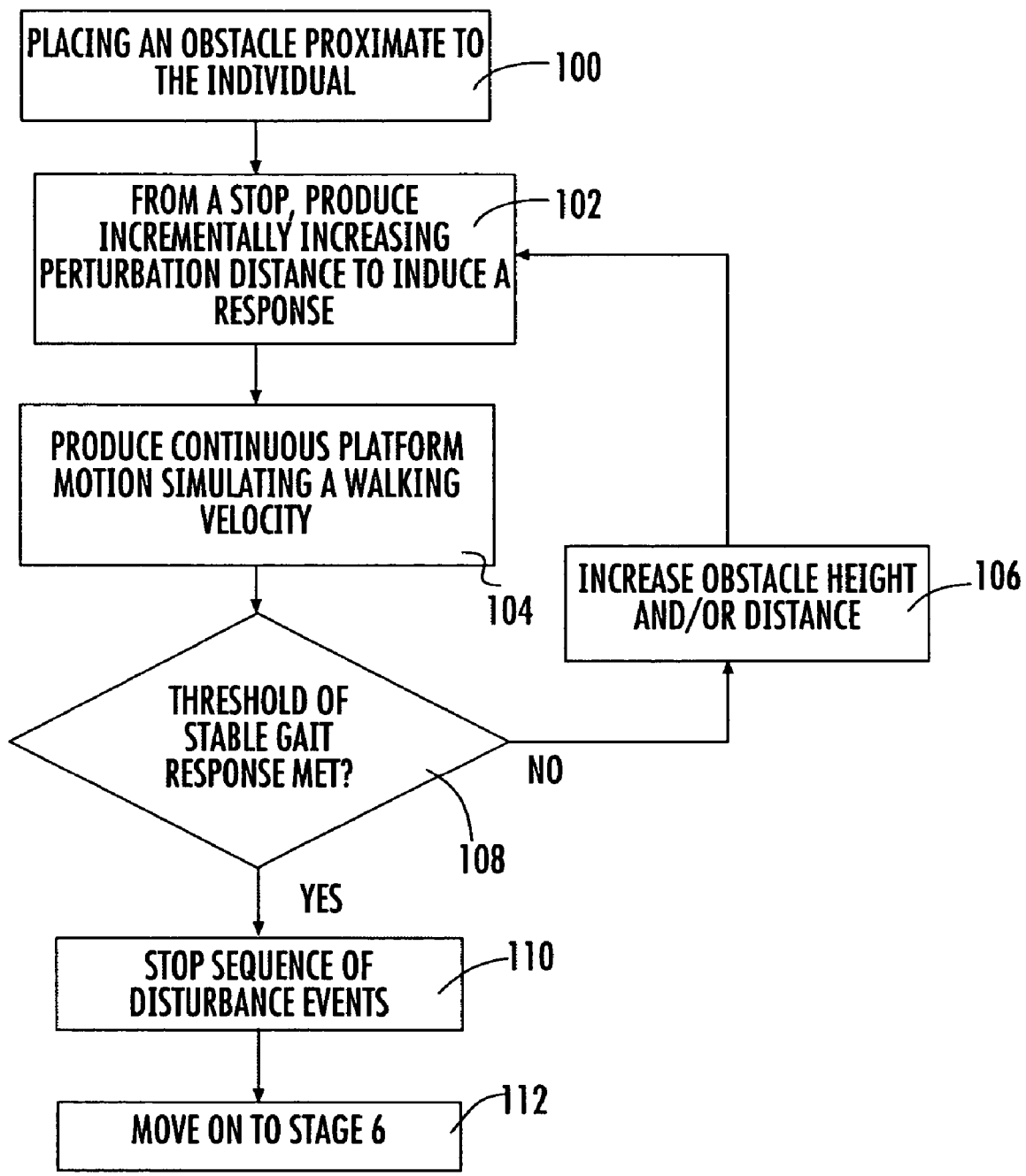
FIG. 12 is a flow chart illustrating the execution of Stage 5 of the method of the present invention.

In FIG. 12, the individual 14 starts at a standstill. A second obstacle is placed proximate to the individual at 100, such as ahead, in the direction such that the perturbation forces them to make a step response. This second obstacle may be the same as the first obstacle but also may be a different obstacle. A large disturbance is introduced at a random time. The disturbance causes the platform to accelerate to a prescribed (non-zero) velocity. This second velocity is called the velocity change. The maximum time for this change in the platform velocity is less than 500 ms, and is more typically in the range of about 100 to about 200 ms.

The distance that the second obstacle is placed from the individual can vary between zero (i.e. touching the individual) and a prescribed maximum obstacle distance from individual. Intrinsic individual parameters, such as height, body center of mass, age, and flexibility are used to determine a maximum obstacle distance or threshold from individual for that individual. As above, the second obstacle can either be real virtual and preferably 5 cm high, although, the obstacle could be in the range of 1 mm up to about one half of the body height of the individual.

A stable gait response is sought in Stage 5. If the individual is able to achieve a stable gait within the predetermined number of steps, the trial is considered successful. If the individual requires more than the predetermined number of steps to achieve stable gait or if the individual falls, the change in velocity is repeated.

Trials are be repeated within a session or across sessions until the variability in step response following a given perturbation displacement and profile are below a target or threshold value. For example, a minimization function relating step length and step width may be employed to calculate a residual value for step response. This value is be called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity change perturbation, that velocity change is increased until individual is able to successfully complete a prescribed velocity change at 108. The height of the obstacle is progressively incrementally increased up to a prescribed height at 106. The initial distance of the second obstacle from the individual is progressively incrementally increased at 102 up to a prescribed distance. Intrinsic individual parameters, such as height, body center of mass, age, and flexibility, are used to determine, for that individual, the maximum velocity change, the maximum obstacle height and the maximum initial obstacle distance for that individual. Once the individual has exceeded the predetermined maximum velocity change with stable gait step response at 108 and acceptably low variability between sessions, the disturbance events are stopped at 110 and they are moved to Stage 6 in the protocol at 112 of the method of the present invention. It should also be noted that in the case where the disturbance event is large and is intended to be a slip incident, Stage 5 may be omitted.

Stage 6—Stable Gait after Initial Steady State Locomotion and Large Disturbance

Figure 13:
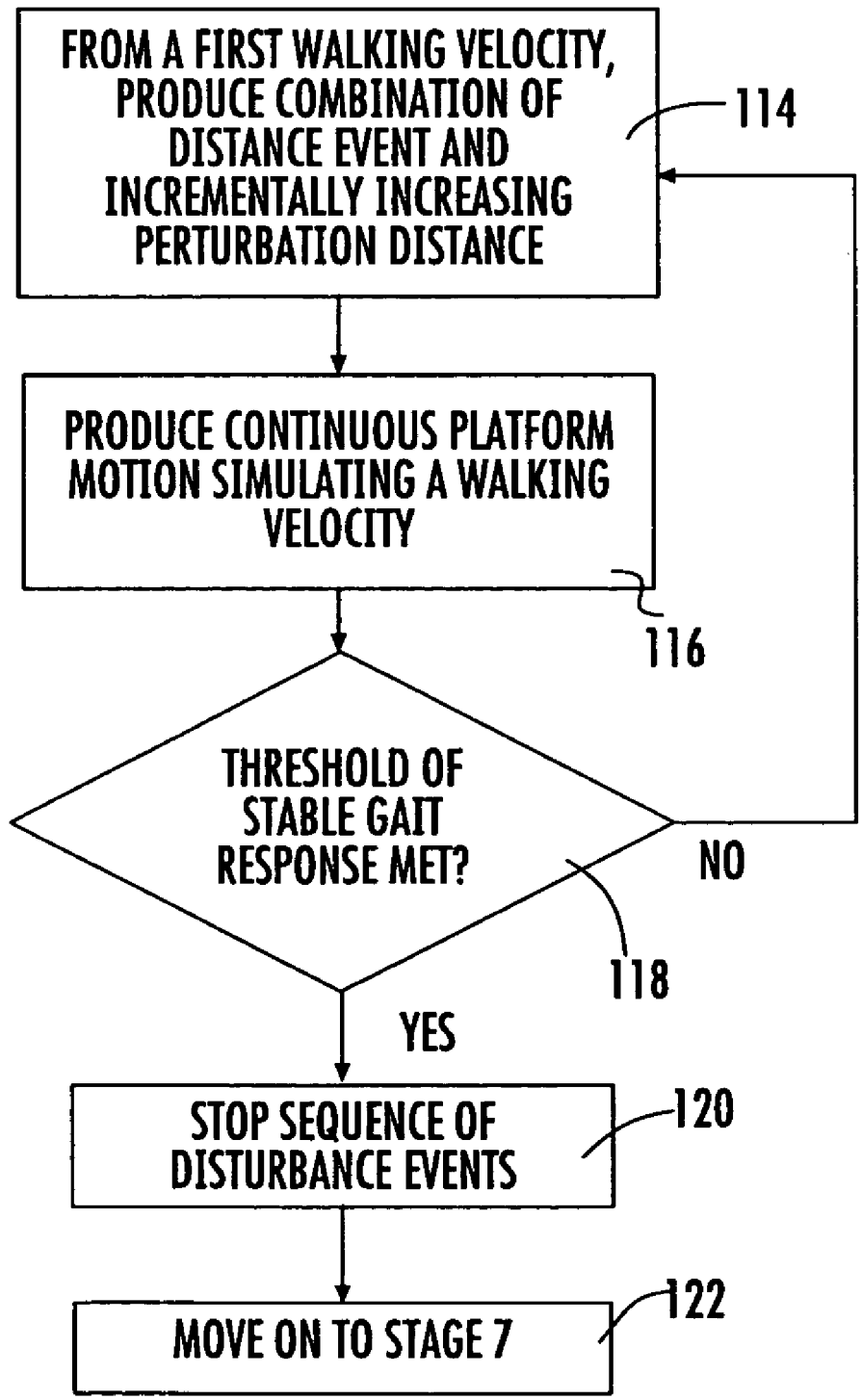
FIG. 13 is a flow chart illustrating the execution of Stage 6 of the method of the present invention.

In FIG. 13, the individual starts at an initial steady state locomotion velocity (velocity 1). A large disturbance is introduced at a random time. The disturbance causes the platform to accelerate to a prescribed disturbance velocity (velocity 2) before returning to a second steady state locomotion velocity (velocity 3). The maximum time for this change in the platform velocity (the time between when the change from velocity 1 is initiated and velocity 3 is achieved) is less than about 500 ms, and is more typically in the range of about 100 to about 200 ms. Velocity 3 may or may not be different from velocity 1. The three velocities and their timing are called the velocity profile.

A stable gait response is sought from the individual. If they are able to achieve a stable gait within a predetermined number of steps, the trial is considered successful. If the individual requires more than the predetermined number steps to achieve stable gait or if the individual falls, the velocity profile is repeated.

Trials are be repeated within a session or across sessions until the variability in step response following a given perturbation displacement and profile are below a target value or threshold. For example, a minimization function relating step length and step width may be employed to calculate a residual value for step response. This value is be called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity profile perturbation, parameters in that velocity profile are incrementally increased until individual is able to successfully complete a prescribed velocity profile. For example, the magnitude of the disturbance (defined as the difference between velocity 1 and velocity 2) is progressively and incrementally increased up at 114 to a prescribed disturbance magnitude, velocity 1 is progressively and incrementally increased up to a prescribed velocity and velocity 3 is incrementally increased up to a prescribed velocity to achieve motion to simulate walking at 116.

Intrinsic individual parameters, such as height, body center of mass, age, and flexibility, are used to determine the final velocity profile for that individual. Once the individual has exceeded the predetermined final velocity profile with stable gait step response at 118, the disturbance events are stopped at 120 and they are moved to Stage 7 in the protocol of the method of the present invention.

Figure 14:
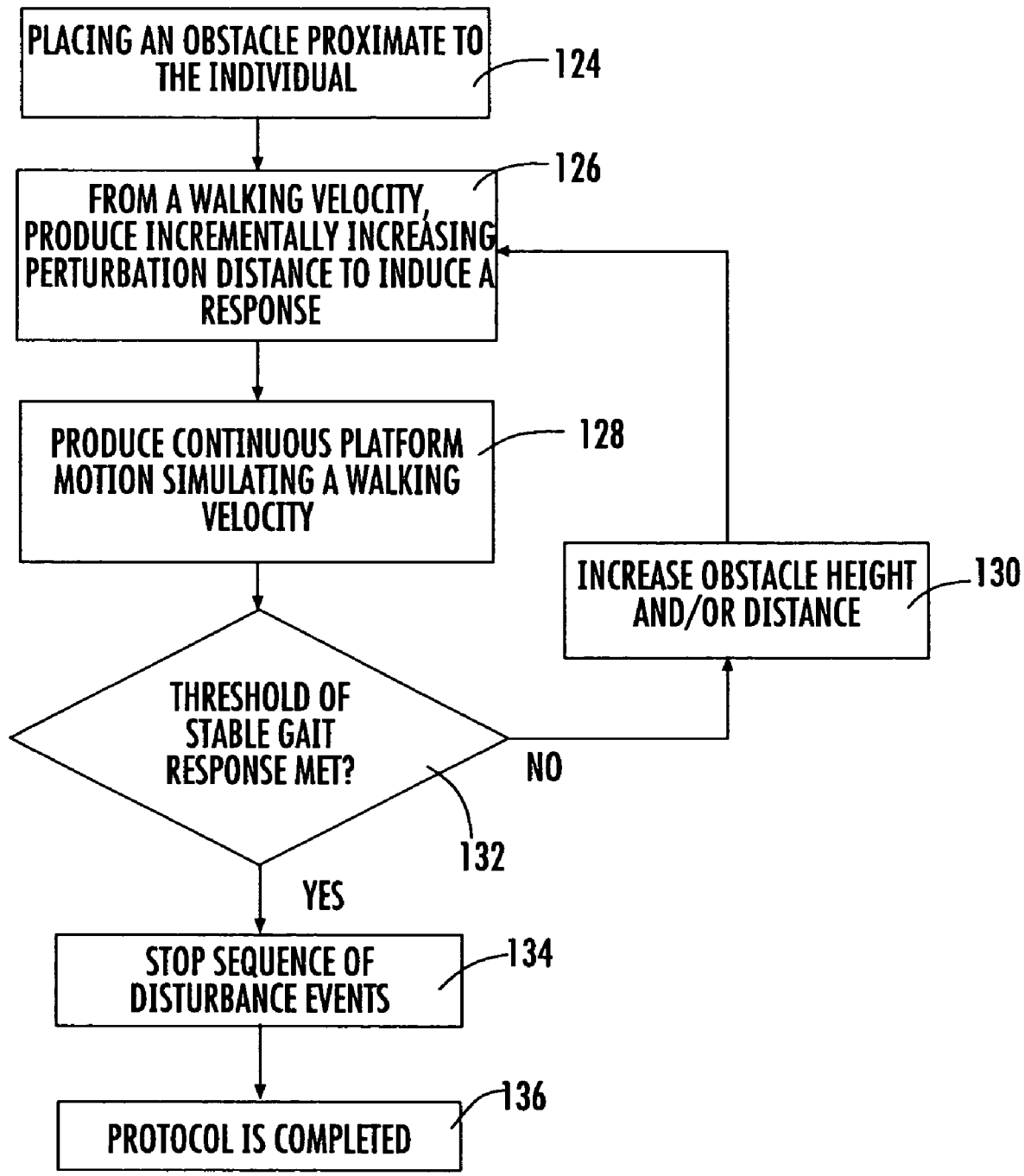
FIG. 14 is a flow chart illustrating the execution of Stage 7 of the method of the present invention.

Stage 7—Stable Gait after Initial Steady State Locomotion and Large Disturbance with Third Obstacle In FIG. 14, the individual 14 starts at an initial steady state locomotion velocity (velocity 1). A large disturbance is introduced at a random time. In concert with the large disturbance, a third obstacle is placed proximate to the individual at 124, such as ahead of the individual, in the direction so that the perturbation forces them to make a step response. The third obstacle may be the same as the first obstacle and/or the second obstacle. Alternatively, all three obstacles may be different than one another. The disturbance causes the platform to accelerate to a prescribed disturbance velocity (velocity 2) before returning to a second steady state locomotion velocity (velocity 3). The maximum time for this change in the platform velocity (the time between when the change from velocity 1 is initiated and velocity 3 is achieved) is less than about 500 ms, and is more typically in the range of about 100 to about 200 ms. Velocity 3 may or may not be different from velocity 1. The three velocities and their timing are called the velocity profile.

The distance that the third obstacle is initially placed from the individual can vary between zero (i.e. touching the individual) and a prescribed maximum obstacle distance from individual. Intrinsic individual parameters, such as height, body center of mass, age, and flexibility are used to determine a maximum obstacle distance from the individual for that individual. Similar to the first obstacle and the second obstacle, the third obstacle can either be real or virtual. In the preferred embodiment of the present invention, the third obstacle is about 5 cm high but it can be in the range of about 1 mm up to about one half of the body height of the individual.

A stable gait response is sought from the individual. If the individual is able to achieve a stable gait within a predetermined number of steps, the trial is considered successful. If the individual requires more than the predetermined number of steps to achieve stable gait or if the individual falls, the velocity profile is repeated.

Trials are be repeated within a session or across sessions until the variability in step response following a given perturbation displacement and profile are below a target value. For example, a minimization function relating step length and step width may be employed to calculate a residual value for step response. This value is called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity profile perturbation, parameters in that velocity profile are incrementally increased until the individual is able to successfully complete a prescribed velocity profile. For example, the magnitude of the disturbance (defined as the difference between velocity 1 and velocity 2) is incrementally increased at 126 up to a prescribed disturbance magnitude to produce a motion simulating a walking velocity at 128. Velocity 1 is incrementally increased up to a prescribed velocity and velocity 3 is incrementally increased up to a prescribed velocity. The height of the third obstacle is progressively increased up to a prescribed height at 130 and the initial distance of the third obstacle from the individual is progressively increased up to a prescribed distance.

Intrinsic individual parameters, such as height, body center of mass, age, and flexibility, are used to determine the final velocity profile (including maximum velocity 1, maximum velocity 2, and maximum magnitude of disturbance), maximum obstacle height, maximum initial obstacle distance for that individual. Once the individual has exceeded the predetermined final velocity profile with stable gait step response at 132 and acceptably low variability between sessions, the disturbance events are stopped at 134 and protocol of the method of the present invention is completed at 136. It should also be noted that in the case where the disturbance event is large and is intended to be a slip incident, Stage 7 may be omitted.

In view of the foregoing, a new and novel system and apparatus is provided that captures biomechanical data of body movement during a disturbance event, such as a slip or trip incident. A disturbance event is simulated by a treadmill-based apparatus. Data collected is used to compute a wide array of parameters associated with body movement to better and more fully understand body movement during a disturbance event. Such parameters are to be studied to determine and evaluate step responses to a disturbance event. As a result, a new and novel method of fall prevention training can be provided to the person to reduce the likelihood of falling following a disturbance event.

It would be appreciated by those skilled in the art that various changes and modifications can be made to the illustrated embodiments without departing from the spirit of the present invention. All such modifications and changes are intended to be covered by the appended claims.

What is claimed is:

1. A disturbance simulation apparatus for fall prevention training of an individual, comprising:
    a perturbation platform movable to create a disturbance event that induces a response from the individual as part of a continuous walking gait; the perturbation platform being a motorized belt and capable of moving to create said disturbance event having a duration of less than 500 ms; the belt enabling the individual to exhibit a continuous walking gait;
    a plurality of sensors located proximate to the individual and the platform;
    data being outputted from the plurality of sensors;
    means for collecting and storing the data during a disturbance event; and
    means for outputting the data.

2. The disturbance simulation apparatus of claim 1, wherein the motion of the motorized belt is bi-directional.

3. The disturbance simulation apparatus of claim 1, wherein the perturbation platform is two motorized bi-directional belts.

4. The disturbance simulation apparatus of claim 1, further comprising:
    an obstacle positioned proximate to the platform to induce the response from the individual to the disturbance event; the obstacle being a disturbance to the gait of the individual.

5. The disturbance simulation apparatus of claim 4, wherein the obstacle is selected from the group consisting of a light beam, a three-dimensional object and a hologram.

6. A method of fall prevention training, comprising the steps of:
    providing a motorized belt platform configured to support an individual standing thereon;
    moving the platform, with the individual thereon, to cause the individual to achieve a continuous walking gait;
    moving the platform to create a disturbance event having a duration of less than 500 ms that induces a step response from the individual as part of a continuous walking gait;
    recording the step response of the individual;
    locating a plurality of sensors proximate to the individual and the platform;
    outputting data from the plurality of sensors;
    collecting and storing the data during a disturbance event; and
    outputting the data.

7. A disturbance simulation apparatus for fall prevention training of an individual, comprising:
    a perturbation platform movable to create a disturbance event that induces a step response from the individual as part of a continuous walking gait; the perturbation platform capable of moving to create said disturbance event having a duration of less than 500 ms; the perturbation platform enabling the individual to exhibit a continuous walking gait.

8. The disturbance simulation apparatus of claim 7, wherein the perturbation platform is a motorized bi-directional belt.

9. The disturbance simulation apparatus of claim 7, wherein the perturbation platform is two motorized bi-directional belts.

10. The disturbance simulation apparatus of claim 7, further comprising:
   an obstacle positioned proximate to the platform to induce the response from the individual to the disturbance event; the obstacle being a disturbance to the gait of the individual.

11. The disturbance simulation apparatus of claim 10, wherein the obstacle is selected from the group consisting of a light beam, a three-dimensional object and a hologram.

12. A method of fall prevention training, comprising the steps of:
   providing a platform configured to support an individual standing thereon;
   moving the platform, with the individual thereon, to cause the individual to achieve a continuous walking gait; and
   moving the platform to create a disturbance event having a duration of less than 500 ms that induces a step response from the individual as part of a continuous walking gait.

* * * * *